United States Patent [19]

Markau

[11] 4,442,830

[45] Apr. 17, 1984

[54] MOUTH DOUCHE

[75] Inventor: Dieter Markau, Murten, Switzerland

[73] Assignee: Gimelli + Co. AG, Zollikofen, Switzerland

[21] Appl. No.: 427,317

[22] Filed: Sep. 29, 1982

[30] Foreign Application Priority Data

Feb. 24, 1982 [DE] Fed. Rep. of Germany ....... 3206843

[51] Int. Cl.³ .............................................. A61H 9/00
[52] U.S. Cl. .................................. 128/66; 128/62 A; 433/80
[58] Field of Search ................. 128/66, 62 A, 200.21; 433/80, 88; 222/321, 402.24

[56] References Cited

U.S. PATENT DOCUMENTS

| | | | |
|---|---|---|---|
| 3,405,710 | 10/1968 | Kovach | 128/62 A |
| 3,703,170 | 11/1972 | Ryckman | 128/68 |
| 3,800,786 | 4/1974 | Kovach | 128/66 |

FOREIGN PATENT DOCUMENTS

| | | | |
|---|---|---|---|
| 2604404 | 8/1977 | Fed. Rep. of Germany | 128/66 |
| 2926309 | 1/1981 | Fed. Rep. of Germany | 128/66 |

OTHER PUBLICATIONS

"The Amazing Home Mouth-Cleaning Machine" (JADA, Mar. 1971).

*Primary Examiner*—John J. Wilson
*Attorney, Agent, or Firm*—Karl F. Ross; Herbert Dubno

[57] ABSTRACT

A mouth douche including a water reservoir, a water pump and a nozzle insertable into the oral cavity is provided with a detachable power unit operable by a preferably rechargeable battery. The power unit advantageously is the body of an electric toothbrush insertable upside down, without its bristle-carrying head, into the base of the mouth douche for operative coupling of its shaft with the water pump.

9 Claims, 2 Drawing Figures

MOUTH DOUCHE

FIELD OF THE INVENTION

My present invention relates to a device for oral hygiene adapted to be used as a mouth douche.

BACKGROUND OF THE INVENTION

Conventional mouth douches generally have a base provided with a water reservoir communicating with a water pump which in turn is connected, generally via extensible flexible tubing, with a hand-held nozzle or applicator designed to be inserted into the oral cavity of a user. In order to drive the pump, a motor in the base is connectable through a suitable adapter and a cable to a utility outlet. Reference in this connection may be made, for example, to a device designated "Water-Pik-Touch-Tonic" toothbrush ZT10 as described on page 206 of Vol. XXII, issue No. 17 (Sept. 1, 1971) of the German periodical for the dental profession termed "Zahnärztliche Praxis".

The use of a water-handling device connected to a high-voltage outlet in a bathroom is not without risks. In fact, a number of countries forbid the presence of such outlets in bathrooms for reasons of safety.

OBJECTS OF THE INVENTION

The general object of my present invention, therefore, is to provide an appliance of this type which can be used without any electrical connection to a utility outlet.

A more particular object is to provide an appliance of this sort which also has another function related to oral hygiene, specifically the cleaning of teeth.

SUMMARY OF THE INVENTION

A device according to my invention comprises a mouth douche of generally conventional character whose base, however, does not contain an electric motor but is instead provided with a socket for the insertion of a battery-operated power unit detachable therefrom. Upon its insertion, the power unit is operatively linked with the water pump by coupling means in the base whereby water will be propelled from the reservoir to the nozzle.

Advantageously, in accordance with a more particular feature of my invention, the power unit comprises a body or stem of an electric toothbrush of the type having a drive shaft adapted to be fitted with a bristle-carrying head. The drive shaft is positively engageable with the coupling means in the base of the mouth douche upon insertion of the body into the aforementioned socket in an upside-down position.

Electric toothbrushes of this nature, powered by batteries, are well known and are widely available on the market. In many instances these batteries are automatically recharged when the hand-held body is placed upright in a holder connected via a cable to a wall outlet, not necessarily in the bathroom in which the toothbrush is to be utilized. My present invention, in its preferred mode of realization, takes advantage of such a toothbrush body as a means for driving the water pump of a mouth douche in addition to its normal function of serving as a carrier for a detachable bristle head. The holder with its recharging connection may be designed as a preferably separable extension of the base of the mouth douche; the toothbrush may also operate on a dry cell or primary battery, rather than on a secondary or rechargeable one, in which case there will of course be no connection to any wall outlet.

In either case, the provision of a common power source for the toothbrush and the mouth douche represents a considerable simplification in such a double-duty appliance, thus reducing its overall cost.

BRIEF DESCRIPTION OF THE DRAWING

The above and other features of my invention will now be described in detail with reference to the accompanying drawing in which.

SPECIFIC DESCRIPTION

Figure 1:
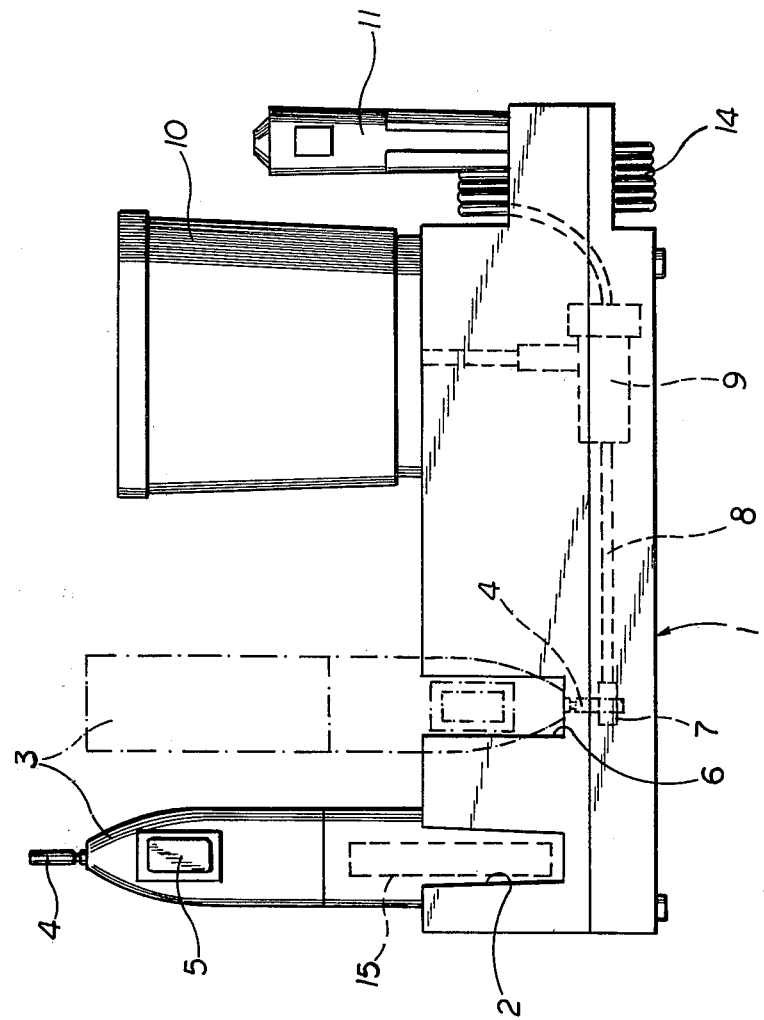
FIG. 1 is a somewhat diagrammatic side-elevational view of a device embodying my invention.

The device shown in FIG. 1 comprises a base 1, designed to rest on a shelf or to be screwed onto a wall in a bathroom, which supports a water reservoir 10 and a hand-held nozzle or applicator 11 of generally conventional structure. A pump 9 inside base 1 has an inlet connected to reservoir 10 and an outlet linked via flexible tubing 14 with nozzle 11, the tubing being coiled into a reel from which it can be elastically payed out when the nozzle is withdrawn from the base.

A socket or seat 2 at an end of base 1 remote from nozzle 11 accommodates the body or stem 3 of an electric toothbrush in an upright position, this stem including a power stage with a battery 15 for imparting rotation and/or axial reciprocation to a drive shaft 4 projecting from its upper end; the operation of the shaft 4 is controlled by a switch 5. A bristle-carrying head to be fitted to shaft 4 for tooth-cleaning purposes has not been illustrated.

Another socket 6 in base 1 is designed to receive the toothbrush stem 3 in an upside-down position, as illustrated in phantom lines, with its drive shaft 4 positively engaging a coupler 7 which is linked by a transmission 8 with water pump 9. Depending on the type of motion executed by drive shaft 4, as well as on the nature of water pump 9 (whether rotary or piston-operated); coupler 7 will have a structure converting the movement of shaft 4 into a pumping action delivering water from reservoir 10 to one or more orifices of nozzle 11; thus, for example, the coupler may include a pawl-and-ratchet drive translating a reciprocating motion into a rotary one.

Figure 2:
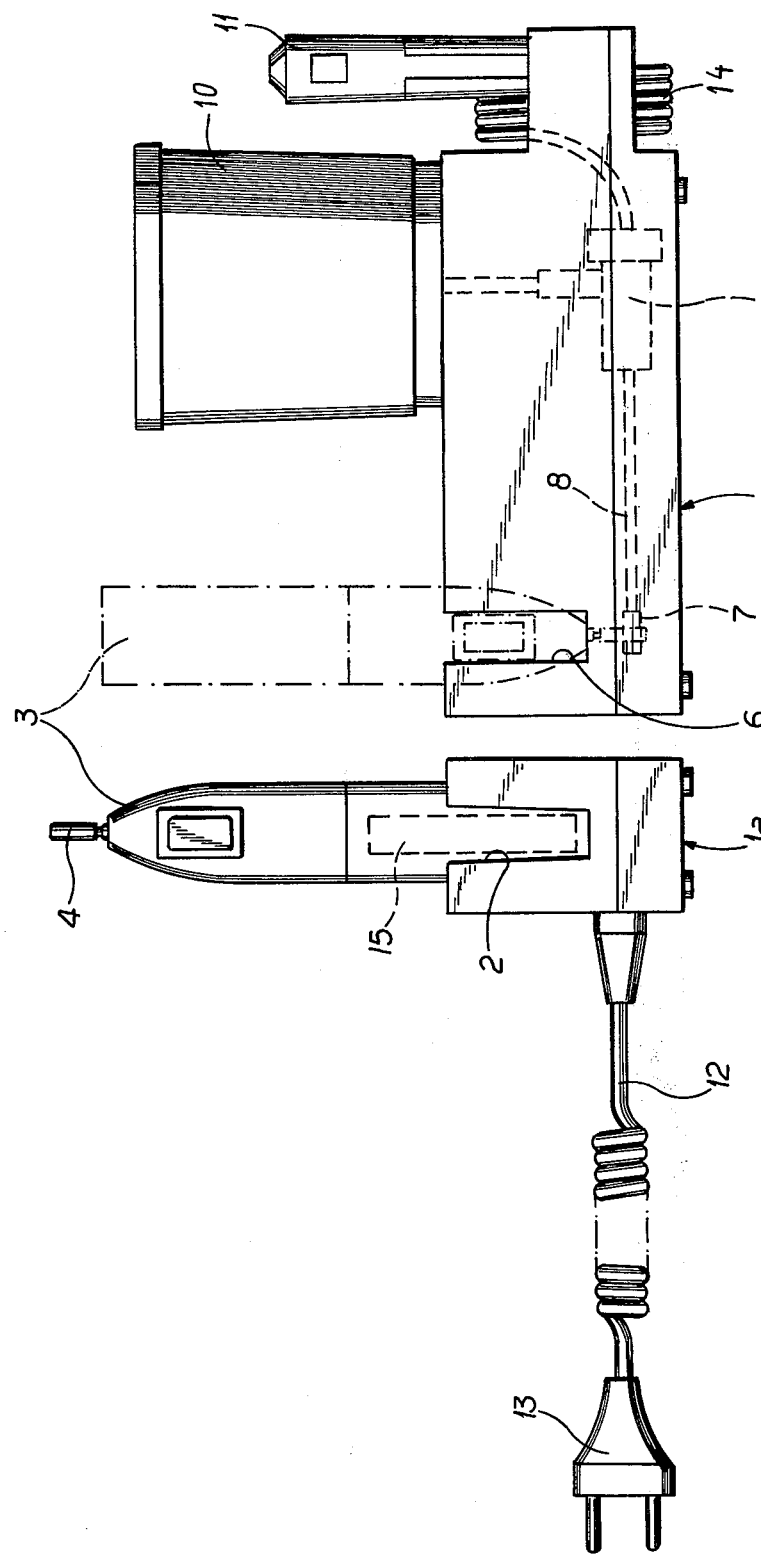
FIG. 2 is a view similar to FIG. 1, illustrating a modification.

In a simplified device, socket 2 could be eliminated and socket 6 may be modified to accommodate the toothbrush assembly including body 3 also in its full-line upright position. In the case of a rechargeable battery, the toothbrush-holding part of base 1 can be equipped with the usual step-down and rectification circuitry connectable through a cable to a wall outlet whereby recharging will take place whenever the self-contained power unit 3 is in the full-line position of FIG. 1. Especially in situations where no utility outlet is available in a bathroom, that part may be designed as a separable extension of base 1 or may be completely independent thereof as illustrated at 1a in FIG. 2; according to this modification, holder 1a formed with socket 2 is provided with a cable 12 terminating in a plug 13. The foreshortened base, equipped only with socket 6 and coupler 7 in addition to the components of the mouth douche, has been designated 1b in FIG. 2.

It should be noted that, even if parts 1a and 1b were structurally integral with each other, there would never exist an electrical connection between the high-voltage side 12, 13 and the pump drive so that the risk of a shock to the user in the event of a malfunction would be greatly reduced. By way of additional precaution, especially where wall outlets in bathrooms are permissible, the user in that case may be instructed to avoid insertion of plug 13 into such an outlet while rinsing his mouth. Such a precaution may also be advisable when, in a simplified device having only one socket for receiving the stem 3 in its upright as well as in its inverted position, the socket is designed to recharge the battery or batteries of the stem in its normal (full-line) position.

I claim:

1. A device for oral hygiene, comprising:
   a mouth douche including a base provided with a water reservoir, a nozzle insertable into the oral cavity of a user, and a water pump in a conduit linking said nozzle with said reservoir;
   a toothbrush assembly including a power unit having a drive shaft having means for operatively connecting a bristle-carrying head thereto, said base being provided with a seat removably accommodating said assembly, said base further having a socket having means for receiving a part of said drive shaft; and
   coupling means in said base engageable with said drive shaft upon insertion of said part thereof into said socket for operatively linking said power unit with said water pump to actuate the latter, said drive shaft being decoupled from said water pump upon removal of said assembly from said base to facilitate the use of said assembly for tooth brushing.

2. A device as defined in claim 1 wherein said socket and said seat are separated from each other on said base, said drive shaft being disengaged from said coupling means upon said assembly being held by said seat.

3. A device as defined in claim 1 or 2 wherein said part is a tip of said drive shaft adapted to be fitted with said bristle-carrying head, said power unit being partly receivable in said socket in an upside-down position.

4. A device as defined in claim 1 wherein said power unit is self-contained with an energy source of its own.

5. A device as defined in claim 4 wherein said energy source is a rechargeable battery.

6. A device for oral hygiene, comprising:
   a mouth douche including a base provided with a water reservoir, a nozzle insertable into the oral cavity of a user, and a water pump in a conduit linking said nozzle with said reservoir;
   a battery-operated power unit detachable from said mouth douche and insertable into a socket of said base; and
   coupling means in said base operatively linking said power unit with said water pump for driving the latter upon insertion of said power unit into said socket, said power unit comprising a body of a battery-powered electric toothbrush having a drive shaft having means for attaching a bristle-carrying head thereto, said drive shaft being engageable with said coupling means upon insertion of said body in an upside-down position into said socket.

7. A device as defined in claim 6 wherein said power unit is provided with a rechargeable battery.

8. A device as defined in claim 7 or 5, further comprising a holder for said power unit provided with recharging means connectable to a utility outlet.

9. A device as defined in claim 8 wherein said holder is an extension of said base.

* * * * *